United States Patent [19]

Plais

[11] Patent Number: 5,368,161
[45] Date of Patent: Nov. 29, 1994

[54] PRESENTING UNIT FOR DENTAL INSTRUMENTATION

[76] Inventor: Marie-Helene Plais, Villa "la Canadienne"-Avenue Sanguet-, le Touquet, France

[21] Appl. No.: 861,454

[22] Filed: Apr. 1, 1992

[30] Foreign Application Priority Data

Feb. 28, 1992 [FR] France .................. 92 02399

[51] Int. Cl.⁵ .................. A61B 19/02; A61C 19/02
[52] U.S. Cl. .................. 206/369; 433/77; 211/69; 206/379; 220/315
[58] Field of Search .................. 433/77, 79; 206/45, 206/63.5, 379, 368, 369, 563; 211/69; 220/315, 324, 326, 338

[56] References Cited

U.S. PATENT DOCUMENTS

| | | | |
|---|---|---|---|
| 1,519,614 | 12/1924 | Heck | 206/45 |
| 1,973,222 | 9/1934 | Moore | 206/369 |
| 2,605,926 | 8/1952 | Casey | 220/338 |
| 3,634,937 | 1/1972 | Green | 433/77 |
| 4,341,312 | 7/1982 | Scholer | 433/77 |
| 4,397,395 | 8/1983 | McKelvey | 433/79 |
| 4,467,947 | 8/1984 | Minneman | 206/379 |
| 4,828,113 | 5/1989 | Friedland et al. | |

FOREIGN PATENT DOCUMENTS

| | | | |
|---|---|---|---|
| 63120 | 8/1968 | German Dem. Rep. | 433/77 |
| 115492 | 12/1929 | Germany | 206/369 |
| 665284 | 9/1938 | Germany | |
| 8614867 | 10/1986 | Germany | |
| 3733524 | 5/1989 | Germany | 206/369 |
| 325660 | 12/1957 | Switzerland | 433/77 |

Primary Examiner—Gene Mancene
Assistant Examiner—Todd E. Manahan

[57] ABSTRACT

The presenting unit (1) comprises a bottom wall (2), two lateral walls (3), a tool-carrying tray (4) placed on the bottom wall between the lateral walls, and a cover (5), the latter and the tray being detachably freely articulated to and hooked on a transverse pivot pin (6) carried by the lateral walls (3). The tray comprises a series of transverse corrugations defining alternating and parallel planes (13,14) inclined relative to the bottom wall. In one of the planes (14) are placed pellets (15) for retaining tools (17 ... 20). Each plane (14) corresponds to a given type of tool. The cover (5) with its bottom wall (2) and lateral walls (3) and the tray (4) can be easily separated after raising the cover. The corrugations of appropriate inclination place the successive rows of tools (17 ... 20) in a position in which they are easily taken hold of by the surgeon. Openings provided in the cover (5), in the bottom wall (2) and at the front and rear of the presenting unit enable the presenting unit and the tools to be sterilized together as an assembly.

12 Claims, 3 Drawing Sheets

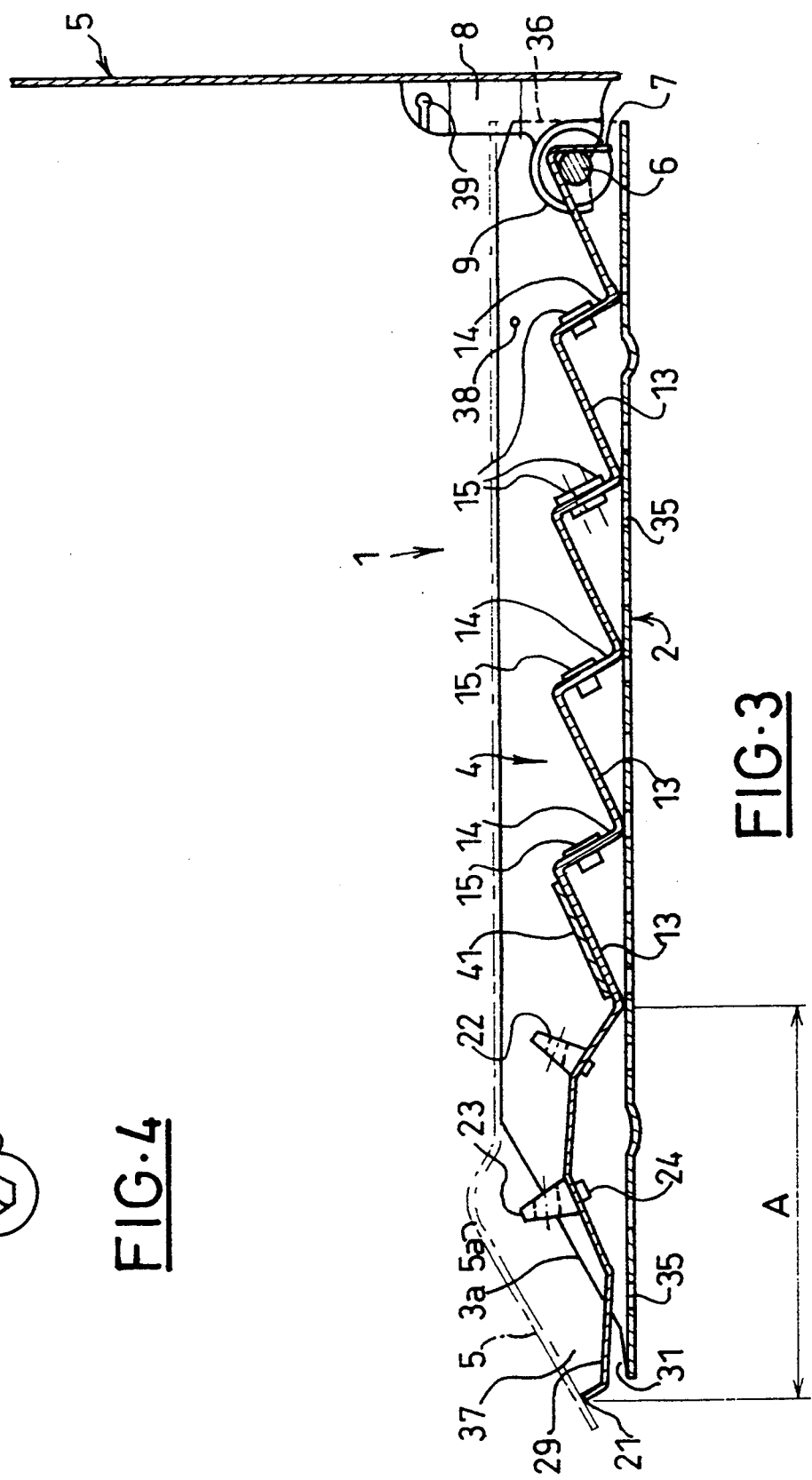

PRESENTING UNIT FOR DENTAL INSTRUMENTATION

The present invention relates to a presenting unit for dental instrumentation.

It is known that dental implantology requires a large number of tools to which the implantologist surgeon must have access when operating. Up to the present time, simple plates acting as trays carrying the tools have been used that the assistant presents to the surgeon in the course of the operation.

This manner of proceeding presents various drawbacks and in particular the risk of errors owing to the fact that each tool is not easily located and is not always easy to take hold of. Further, it is materially impossible to present to the surgeon on a simple support plate a complete set of tools for all the types of implantations capable of being carried out, and the support plate and the tools must be separately sterilized before any operation, which requires multiple manipulations.

An object of the invention is to overcome these drawbacks.

The presenting unit comprises a bottom wall provided with two parallel lateral walls, a tool-carrying tray so dimensioned as to be capable of being disposed on the bottom wall between the lateral walls, and a cover.

According to the invention, the cover and the tray are freely and detachably articulated to and hooked on an end transverse pivot pin carried by the lateral walls, so that, at the end of a rotation, the cover automatically becomes separated from the tray, the latter comprising a series of transverse corrugations defining two groups of alternating planes which are parallel to each other and inclined relative to the bottom wall, in one of which groups of planes are provided means for receiving and retaining the tools, each plane corresponding to a given type of tool.

The presenting unit constructed in this way constitutes a flat case of small overall size whose cover and tray may be very easily separated from the bottom wall, the separation of the cover being automatic at the end of its rotation on its support pin.

The bottom wall and the lateral walls, the tool-carrying tray and the cover are therefore not connected by any fixed connecting means and may be easily separated merely by pivoting the cover and the tray.

The required tools may be disposed on the tray in parallel transverse rows, there being one type of tool per row, which facilitates identification. Advantageously, the order of the rows corresponds to the order of utilization of the tools by the surgeon, the first tools used being the most remote from the surgeon and the last the closest to the surgeon.

The cover and the lateral walls may be so arranged that they define with the bottom wall openings at the opposite ends of the bottom wall and the cover, these openings allowing the steam of a sterilizer to pass through the presenting unit equipped with its tools.

In this way, the presenting unit and its tools may be introduced in and withdrawn from the sterilizer in a single handling operation, which considerably reduces the manual manipulations heretofore required.

Further features and advantages of the invention will be apparent from the following description, with reference to the accompanying drawings which illustrate an embodiment of the invention as a non-limitative example.

FIG. 3 is a longitudinal sectional view taken on line 3—3 of FIG. 2, the cover being shown mounted on its pivot pin and in a raised position.

FIG. 4 is an elevational view to an enlarged scale of one of the retaining elements for the tools of the presenting unit of FIGS. 1 to 3.

Figure 1:
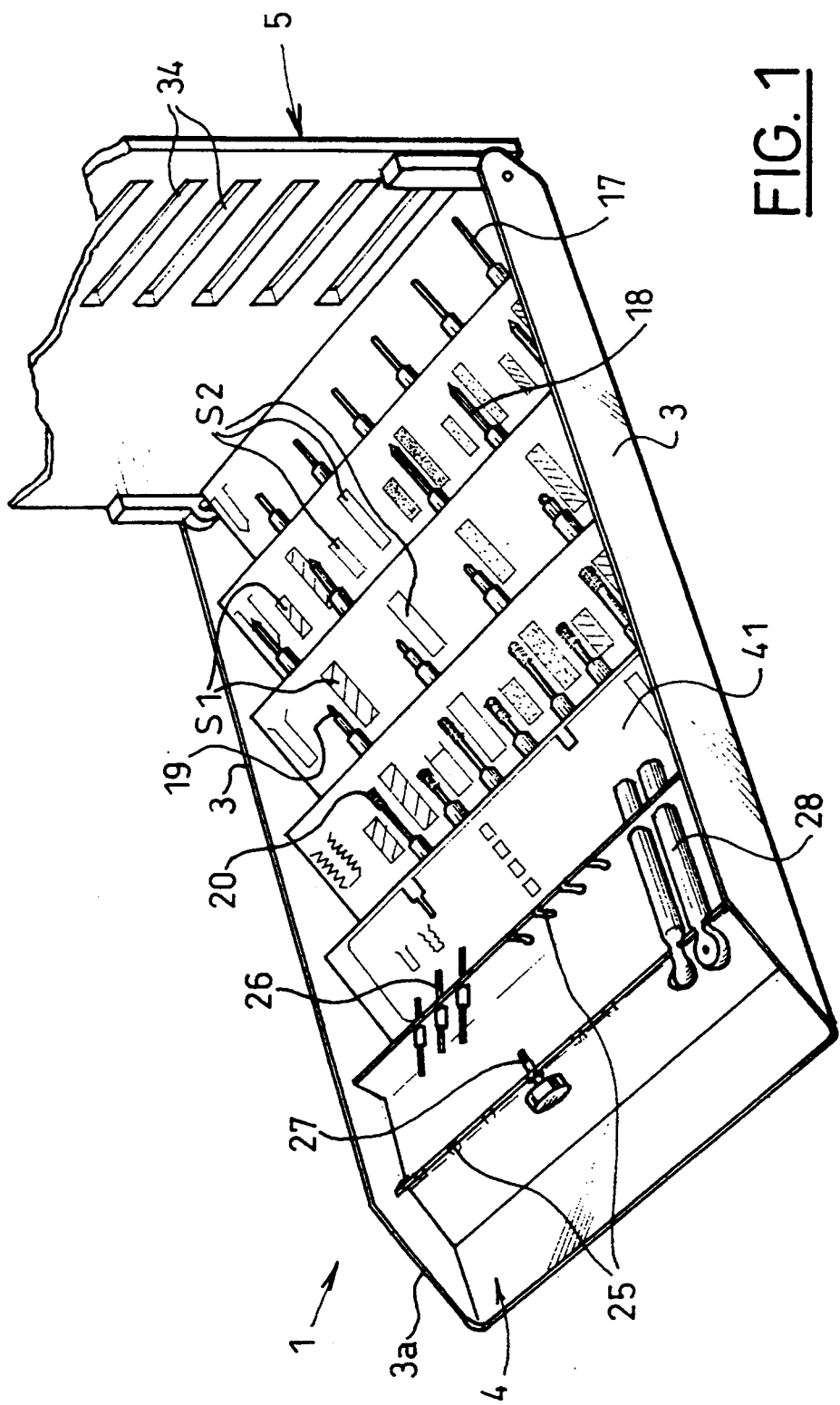
FIG. 1 is a perspective view of an embodiment of the presenting unit for dental instrumentation according to the invention, whose cover has not been shown and whose tray is equipped with several series of tools.

The presenting unit 1 for dental instrumentation shown in the drawings mainly comprises three parts: a preferably rectangular bottom wall 2 provided with two parallel lateral walls 3 on preferably its longitudinal edges, a tool-carrying tray 4 so dimensioned as to be capable of being disposed on the bottom wall 2 between the walls 3, and a cover 5.

The cover 5 and the tray 4 are freely articulated and hooked in a detachable manner on a transverse pin 6 interconnecting the walls 3 at one of their ends. For this purpose, the tray 4 comprises a bent end portion 7 for hooking onto the pin 6, on which the tray rests, and the cover 5 is provided with two fittings 8 to each of which a substantially C-shaped hook 9 is fixed. These hooks 9 are adapted to be placed over the ends of the pin 6 in grooves 11 each defined by a pair of side walls 12 in which the pin 6 is fixed, notches being provided for this purpose in the top parts of the tray 4 adjacent to the pin 6.

The open part of the hooks 9 has a width substantially equal to the diameter of the groove 11.

Consequently, the cover 5 and the tray 4 may be very easily separated from the bottom wall 2 merely by raising them, the separation occurring automatically at the end of the rotation, as shown in FIG. 3 for the cover 5.

The tray 4 comprises a series of transverse corrugations defining, between two consecutive fold lines, two groups of alternating planes 13, 14 which are parallel to one another and inclined with respect to the bottom wall 2. Thus, the planes 14 have a rather large inclination with respect to the bottom wall, for example of the order of 60°, while the planes 13 interposed between the planes 14 have a smaller inclination with respect to the bottom wall 2, for example of the order of 30°. The angle at the apex between two consecutive planes 13, 14 is a right angle, for the aforementioned angles 30° and 60°. These angles are of course given only by way of a non-limitative example and may vary widely.

In the illustrated embodiment, four planes 14 are provided in the tray 4 and extend from one wall 3 to the other, the end hooking portion 7 extending the end plane 13. Each plane 14 is provided with means for receiving and retaining tools, one type of tool being provided per plane 14. In the embodiment illustrated in the drawings, these means are formed by pellets 15 which are engaged in corresponding orifices provided in each plane 14 and have an axial bore 16 (FIG. 4) for receiving tools 17, 18, 19, 20. The bore 16 advantageously has a polygonal cross-sectional shape, for example a hexagonal cross-sectional shape. The pellets 15 are made from a plastics material preferably having a low coefficient of friction, such as "Teflon".

The tray 4 comprises, between the inclined planes 13, 14 and its front edge 21 opposed to the end portion 7, a region A for complementary instruments. In the embodiment illustrated in the drawings, this region A is equipped with two section members 22, 23 which extend transversely along strips of different appropriate inclinations, between the walls 3, and are fixed to the tray 4 by any suitable means, such as rivets 24. Formed in these section members 22, 23 are slots 25 adapted to receive tools 26, 27, 28, an end area 29 extending between the section member 23 and the front edge 21 of the tray. The whole of the region A is so shaped that, when the tray 4 rests on the bottom wall 2, a gap 31 remains between the area 29 and the bottom wall 2 (FIG. 3).

The section members 22, 23 and their supporting strips are so shaped as to present to the surgeon the tools 26, 27, 28 with a suitable inclination which facilitates taking hold of these tools.

Figure 2:
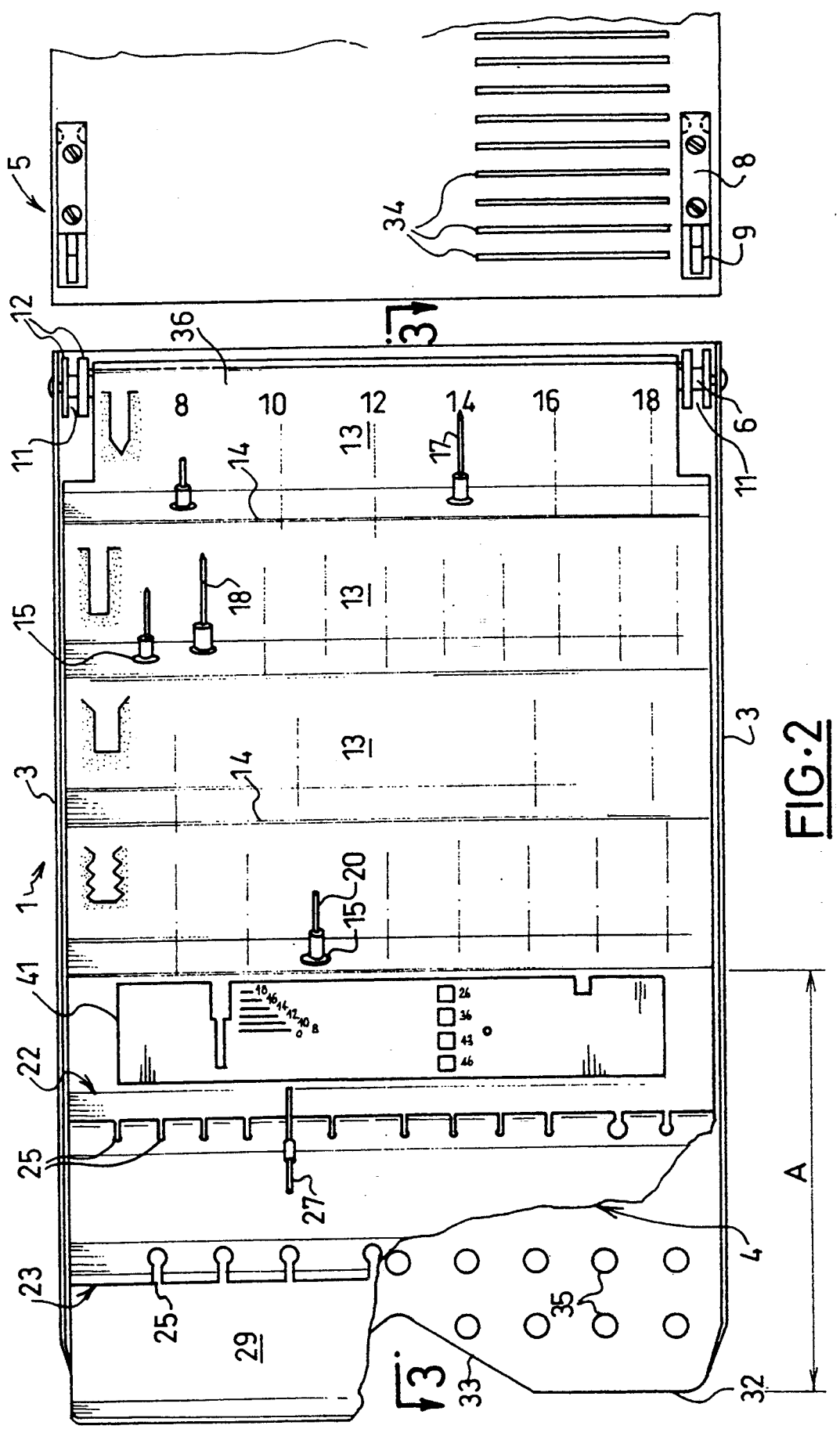
FIG. 2 is a top plan view to an enlarged scale with parts cut away of the presenting unit of FIG. 1, the cover being shown separated from the bottom wall and the tool-carrying tray.

Preferably, the front edge 32 of the bottom wall 2 has a median notch 33 (FIG. 2) adapted to make it easier for the surgeon or his assistant to take hold of the tray.

The bottom wall 2 and the cover 5 are apertured, for example, as shown, by a series of parallel slots 34 provided in the cover 5 and apertures 35 provided in the bottom wall 2. Further, the cover 5 is so shaped that, in the closing position, it delimits with the bottom 2 and the lateral walls 3 an opening 36 in the region of the pivot pin 6 and, at the opposite front end of the bottom wall 2 and the cover 5, two lateral openings 37 (FIG. 3).

To provide these lateral inlets/outlets or openings 37, the front ends 3a of the walls 3 opposed to the pivot pin 6 are inclined with respect to the bottom wall 2. In the presently-described embodiment, for the same purpose the front edge portion 5a of the cover 5 is so bent and inclined as to delimit the openings or inlets/outlets 37 with the ends 3a. A boss 38 is provided on the inner surface of each wall 3 in the vicinity of the pivot pin 6 (FIG. 3) and, in each fitting 8 of the cover 5, an associated orifice 39 is provided for receiving the corresponding boss 38 and retaining the cover 5 in its closing position.

The tools constituting the instrumentation placed in the presenting unit 1 are positioned in a plurality of rows, namely, in the illustrated embodiment and starting at the rear end, i.e. at the pivot pin 6: on the first inclined plane 14, a row of drills 17, then on the following inclined plane 14, a row of reamers 18, on the third inclined plane 14, a row of spot-facing milling tools 19 adapted to form the cylindro-conical part of the hole drilled in the bone pit, then, on the fourth support plane 14, a row of taps 20. The axes of the bores 16 receiving the tools are substantially parallel to the planes 13 and therefore have the same inclination with respect to the bottom wall 2, for example 30° as already mentioned, so as to facilitate taking hold of these tools. Provided on each inclined plane 13 extending under a row of tools are references (numbers 8, 10 . . . 18 on the first plane 13), or reference colours corresponding to an identical section. Thus there may be a plurality of sections of different colours such as S1, S2 . . . spaced apart on the different inclined planes 13 corresponding to the respective rows of tools: the surgeon knows that to use for example the spot-facing milling tool 19 or the tap 20 of red colour, he must first of all use in succession the reamers 18 of yellow colour, then green, then white and lastly red.

There may be disposed on the inclined plane 13 located between the section member 22 and the first plane 14, a detachable checking ruler 41 for additional checkings carried out in the known manner which therefore does not require a particular description. Lastly, the tools 26, 27, 28 may be checking instruments such as, respectively, parallelism gauges, profile gauges, screwing instruments (screwdriver, ratchet spanner, extension for manual screwing or tapping, etc.). These instruments, engaged in the slots 25, are aligned transversely and horizontally in two rows. In the front part of the tray 4, the area 29 permits placing tools thereon or manually taking hold of the tray 4, this taking hold of the tray being facilitated by the central notch 33 and by the fact that the edge portion 21 of the tray is bent upwardly.

The provision of apertures 34, 35 in the bottom wall 2 and the cover 5, front lateral openings 37 and the opening 36 in the region of the pin 6, provides as many passages for the steam (at about 140° C.) through the presenting unit 1 when the latter is placed in a sterilizer. This combination of passages enables the steam to pass through the presenting unit both horizontally and vertically. The assembly comprising the presenting unit and the tools 17 . . . 28 may be positioned in the sterilizer and withdrawn from the latter in a single operation, thereby avoiding the multiple manipulations heretofore required in the absence of any adapted presenting unit.

Advantageously, in order to better locate each drilling tool 17 and avoid blunting their points, these tools are placed in front of a locating and identification plate fixed to the inclined plane 13 adjacent to the bent end portion 7.

The fact of providing a polygonal cross-sectional shape, for example a hexagonal shape 16, in the pellets 15 reduces the contact and therefore the rubbing of the edge of the bore with the stem of the tools and furthermore facilitates the entry of the steam during the sterilization in that gaps forming passages are provided between the stems and the contour of the bores 16.

When the cover 5 is pivoted beyond its vertical position, the hooks 9 leave their grooves 11 and the cover 5 is easily disconnected from the tray 4. The latter, retained solely in translation by its end portion 7, can also be very easily disengaged from its pivot pin 6. When the cover 5 is swung over onto the walls 3, it is maintained in the closing position by the lateral bosses 38 forcefully engaged in the orifices 39. The cover 5, the tray 4 and the bottom wall 2 may advantageously be metallic, for example composed of shot-peened anodized aluminium, the section members 22, 23 being for example of an elastomer.

The small overall size of the presenting unit enables a plurality of units to be stored one on top of the other. With the presenting unit just described, each tool is easily locatable with no possibility of error, can be easily taken hold of and placed back in position after use and the surgeon has available a complete set of tools for any type of implantation required. Further, the assembly comprising the presenting unit and the tools may be perfectly sterilized before any operation in a single handling thereof. The elements of the presenting unit which become of no use and get in the way during the operation may easily be removed after having been placed on the front area 29, the tray 4 being moreover easily taken hold of by the assistant or the surgeon independently of the other elements of the presenting unit.

Many alternative arrangements of the invention may be envisaged, for example as concerns the number of corrugations and therefore rows of tools, the inclination of the planes 13 and 14, the arrangement of the apertures 34, 35 and the openings for the passage of the sterilization steam at the front and at the rear of the presenting unit, the replacement of the pellets 15 by any other adapted means, the arrangement of the front region A, etc.

What is claimed is:

1. Presenting unit for dental instrumentation, said unit comprising a bottom wall, two parallel lateral walls connected to said bottom wall, a tool-carrying tray so dimensioned as to be capable of being placed on said bottom wall between said lateral walls, a cover, and a transverse pivot pin carried by said lateral walls adjacent an end of said lateral walls, said cover being freely articulated to, and said tray being freely hooked on, said pivot pin in a detachable manner, so that, at the end of a pivoting of said cover about said pivot pin, said cover is automatically separated from said tray, said tray comprising a series of transverse corrugations defining a first group of planes and a second group of planes which are in alternating and parallel relation and inclined relative to said bottom wall, means for receiving and retaining tools being provided in said second planes, each second plane corresponding to a given type of tool.

2. Presenting unit according to claim 1, wherein each articulating connecting said cover to said lateral walls comprises a pair of side walls connected to an end of said pivot pin and defining a groove, and a substantially C-shaped hook placed at an end of a fitting fixed to said cover.

3. Presenting unit according to claim 2, wherein said hook of each articulation has an open part having a width substantially equal to the diameter of said groove.

4. Presenting unit according to claim 1, wherein said cover and said lateral walls are so arranged as to define with said bottom wall openings for the passage of steam at opposite ends of said bottom wall and said cover.

5. Presenting unit according to claim 1, wherein said corrugations of said detachable tray define consecutive alternating first planes and second planes which make with said bottom wall angles respectively substantially 30° and 60°, an apex angle formed by said first planes and second planes being substantially a right angle.

6. Presenting unit according to claim 1, wherein said tray comprises, between said inclined second planes and a front edge of said tray opposed to said end of said lateral walls, a region reserved for complementary instruments, said region being so shaped as to define with said bottom wall a free gap when said tray rests on said bottom wall.

7. Presenting unit according to claim 1, comprising means for retaining said cover in a closing position of said cover.

8. Presenting unit according to claim 7, wherein said means for retaining said cover comprise bosses provided on said lateral walls in the vicinity of said pivot pin and associated orifices provided in said cover for receiving said bosses.

9. Presenting unit according to claim 1, wherein said means for retaining tools comprise pellets defining an axial bore for receiving said tools, apertures being provided in said tray and said pellets being engaged in said apertures.

10. Presenting unit according to claim 9, wherein said axial bore has a polygonal cross-sectional shape.

11. Presenting unit according to claim 9, wherein said pellets are composed of a plastics material having a low coefficient of friction.

12. Presenting unit according to claim 1, wherein said tray has a bent end hooking portion which bears on said transverse pivot pin.

* * * * *